United States Patent
Blacker

(10) Patent No.: US 7,408,082 B1
(45) Date of Patent: Aug. 5, 2008

(54) RACEMISATION PROCESS

(75) Inventor: John Blacker, Huddersfield (GB)

(73) Assignee: NPIL Pharmaceuticals (UK) Limited, Huddersfield (GB)

( * ) Notice: Subject to any disclaimer, the term of this patent is extended or adjusted under 35 U.S.C. 154(b) by 0 days.

(21) Appl. No.: 11/836,422

(22) Filed: Aug. 9, 2007

(51) Int. Cl.
*C07B 57/00* (2006.01)

(52) U.S. Cl. .................................................. 564/302

(58) Field of Classification Search ........................ None
See application file for complete search history.

(56) References Cited

FOREIGN PATENT DOCUMENTS

| WO | WO-92/15552 | 9/1992 |
|---|---|---|
| WO | WO-2005/023752 A2 | 3/2005 |

*Primary Examiner*—Samuel A Barts
(74) *Attorney, Agent, or Firm*—Dana M. Gordon; Foley Hoag LLP

(57) ABSTRACT

The present invention relates to a novel process for obtaining (1S,4S)N-methyl-4-(3,4-dichlorophenyl)-1,2,3,4-tetrahydro-1-naphthaleneamine from a mixture of its isomers. The process involves isomerising the 1-position and the 4-position and effecting separation of the desired isomer by methods such as fractured crystallization. The process can be operated as a continuous process.

20 Claims, No Drawings

RACEMISATION PROCESS

BACKGROUND OF THE INVENTION

Sertraline has two chiral centres and hence has four stereoisomeric forms, namely, the (1R,4R), (1S,4S), (1R,4S), and (1S,4R) isomeric forms of sertraline. Of these, the active stereoisomer for therapeutic purpose is the cis (1S,4S) isomer of formula 1.

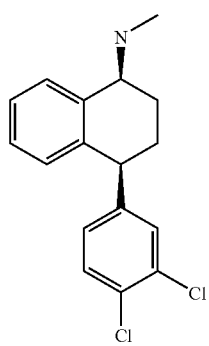

(1)

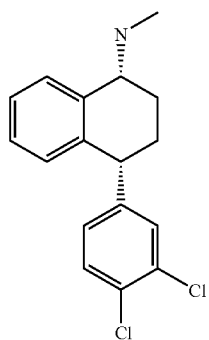

(2)

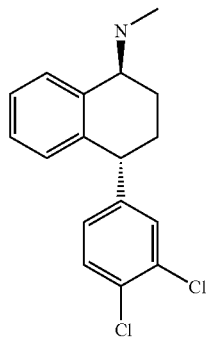

(3)

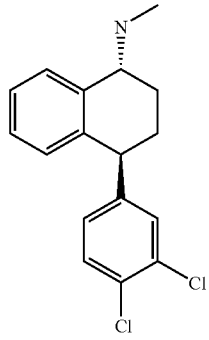

(4)

Although a number of processes have been described for the production of setraline or intermediates used in the production of setraline, see U.S. Pat. No. 4,536,518, U.S. Pat. No. 4,556,676, U.S. Pat. No. 4,777,288 U.S. Pat. No. 4,839,104, WO98/15516, U.S. Pat. No. 5,196,607, U.S. Pat. No. 5,466,880, Tetrahedron, 48(47), 10239 (1992), WO95/15299, WO98/27050, Organic Lett., 1(2), 293 (1999), in all the methods described, eventual isomer separation is inevitable. These documents describe processes for producing sertraline and the disclosures in these documents illustrate the problems in producing optically pure sertraline and the resulting low yields and waste that arises due to production of unwanted isomers.

In U.S. Pat. No. 5,082,970 there is described a process for recycling the trans isomer of sertraline. However, this process appears only to isomerise only one of the two chiral centres of the trans isomer of sertraline.

In WO01/49638 and WO05/023752 there are described processes for the isomerisation of both chiral centres of setraline isomers. WO01/49638 requires that the amine first be oxidised to an imine. This imine intermediate is subjected to an isomerisation process at the benzylic chiral centre and then subsequently reducing the imine non-stereospecifically. WO05/023752 seeks to isomerise the benzylic chiral centre first before subjecting the amine to oxidation and reduction either directly of the imine or indirectly by reaction of the ketone with an amine and reduction of the imine so produced. Both of these methods suffer from the disadvantage that oxidation of amines to imines is difficult and not only requires the use of strong oxidants in stoichiometric amounts but often results in the production of unwanted ketone which adds to the complexity of the recycle.

It is therefore, the object of the present invention to develop an alternate simple process whereby the unwanted isomers, can be recycled to produce the desired cis (1S,4S) isomer in a simple manner which is commercially feasible.

SUMMARY OF THE INVENTION

The present invention relates to a novel process for obtaining (1S,4S)N-methyl-4-(3,4-dichlorophenyl)-1,2,3,4-tetrahydro-1-naphthaleneamine, commonly known as sertraline. Sertraline is generally prepared in the form of its hydrochloride salt, from stereoisomers thereof, for example, the cis (1R,4R) isomer [(1R,4R)N-methyl-4-(3,4-dichlorophenyl)-1,2,3,4-tetrahydro-1-naphthaleneamine], the trans (1S,4R) isomer, or the trans (1R,4S) isomer, or mixtures or salts thereof. The isomers other than (1S,4S) are undesired stereoisomers of sertraline, and they are invariably co-produced during the manufacture of this drug by known processes, such as that disclosed in U.S. Pat. No. 4,536,518 and U.S. Pat. No. 4,556,676. The present invention also relates to a novel process for recycling the undesired stereoisomers produced during manufacture by an iterative process to increase the overall yield of sertraline.

DETAILED DESCRIPTION OF THE INVENTION

The present invention relates to a novel process for obtaining (1S,4S)N-methyl-4-(3,4-dichlorophenyl)-1,2,3,4-tetrahydro-1-naphthaleneamine (the compound of formula 1), commonly known as sertraline. Sertraline is generally prepared in the form of its hydrochloride salt, from stereoisomers thereof, for example the cis (1R,4R) isomer of formula 2 [(1R,4R)N-methyl-4-(3,4-dichlorophenyl)-1,2,3,4-tetrahydro-1-naphthaleneamine], the trans (1S,4R) isomer of formula 3, or the trans (1R,4S) isomer of formula 4, or mixtures or salts thereof.

(1)

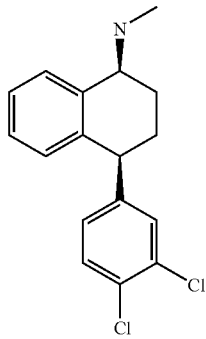

(2)

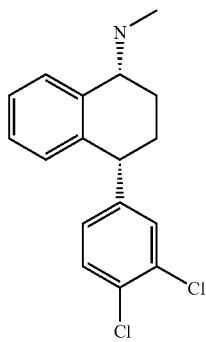

(3)

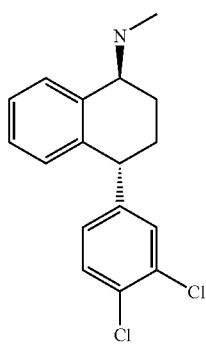

(4)

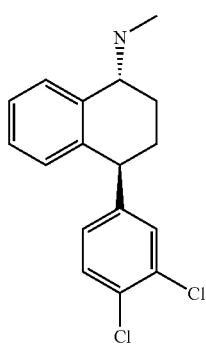

These isomers of formulas 2, 3 and 4 are undesired stereoisomers of sertraline of formula 1, and are invariably co-produced during the manufacture of this drug by known processes such as that disclosed in U.S. Pat. No. 4,536,518 and U.S. Pat. No. 4,556,676.

More particularly, the present invention relates to a novel process for recycling the undesired stereoisomers produced during manufacture by an iterative process to increase the overall yield of sertraline.

In one aspect of the present invention, there is a process for isomerising the C-4 position of N-methyl-4-(3,4-dichlorophenyl)-1,2,3,4-tetrahydro-1-naphthaleneamine using a transition metal catalyst and optionally a promoter.

According to another aspect of the present invention there is provided a process for obtaining (1S,4S)—N-methyl-4-(3, 4-dichlorophenyl)-1,2,3,4-tetrahydro-1-naphthaleneamine from at least one isomer selected from (1R,4R)—N-methyl-4-(3,4-dichlorophenyl)-1,2,3,4-tetrahydro-1-naphthaleneamine, (1S,4R)—N-methyl-4-(3,4-dichlorophenyl)-1,2,3,4-tetrahydro-1-naphthaleneamine, or (1R,4S)—N-methyl-4-(3,4-dichlorophenyl)-1,2,3,4-tetrahydro-1-naphthaleneamine the process comprising treating the isomer or mixture of isomers with (1) a reaction system operative to isomerise the C-4 position; and (2) a transition metal catalyst system and optionally a reaction promoter operative to isomerise the C-1 position.

In one embodiment, the process includes the steps of initially isomerising the C-4 position and in a subsequent step isomerising the C-1 position. In an alternative embodiment, the process includes the step of isomerising the C-1 position and in a subsequent step isomerising the C-4 position.

The reaction system is one or more reagents which together are effective to isomerise the C-4 chiral centre. Preferably when an initial mixture deficient in isomers with a 4S chiral centre is treated with an isomerising system the ratio of 4S to 4R isomers present is increased.

The catalyst system includes and catalyst system which can isomerise the C-1 chiral centre. Preferably when an initial mixture deficient in isomers with a 1S chrial centre is treated with a catalyst system the ratio of 1S to 1R isomers present is increased.

More, preferably the initial mixture is one which is deficient in the 1S,4S isomer. Mixtures which are referred to as ones deficient in isomers, include those mixtures wherein the concentration of the isomer referred to is less than that predicted for mixtures wherein the chiral centres are allowed to freely isomerise and reach equilibrium under thermodynamic control.

Treatments (1) and (2) may be carried out sequentially, in separate steps, and in any order. Alternatively, treatments (1) and (2) may be carried out together, in a single step.

Following or during the treatments (1) and (2), the (1S,4S)-isomer is separated from the reaction mixture, by any method known in the art, e.g., by fractional crystallization, resolution, chiral separations, diastereomer separations or combinations thereof. Thereafter or simultaneously, any unwanted (1S,4R), (1R,4R) or (1R, 4S) isomers are retreated with (1) and (2) in an iterative procedure so that the (1S,4S)-isomer so produced is isolated and results in a reduction of unwanted isomers and improved overall yield of the desired isomer.

The process described in this invention permits convenient recycling of the unwanted steroisomers of sertraline on a commercial scale as the entire process is simple and requires inexpensive raw materials.

In one preferred embodiment, the initial reaction mixture comprises predominantly the cis (1R,4R) stereoisomer of sertraline, with respect to any other individual isomer that may be present. For example in addition to the cis (1R,4R), one or more of the cis (1S,4S) the trans (1S,4R) or trans (1R,1S) stereoisomer of sertraline may also be present, however the concentration of cis(1R,4R) need only exceed the concentration of each isomer individually.

In another preferred embodiment, the initial reaction mixture comprises predominantly trans stereoisomers of sertraline with respect to any cis isomer present. For example, the initial reaction may comprise one or more trans isomers which individually or together predominate over any cis isomers that may also be present.

The isomer or mixture of isomers comprising at least one isomer selected from (1R,4R)—N-methyl-4-(3,4-dichlorophenyl)-1,2,3,4-tetrahydro-1-naphthaleneamine, (1S,4R)—N-methyl-4-(3,4-dichlorophenyl)-1,2,3,4-tetrahydro-1-naphthaleneamine, or (1R,4S)—N-methyl-4-(3,4-dichlorophenyl)-1,2,3,4-tetrahydro-1-naphthaleneamine may contain an inorganic acid such as hydrochloric acid, or an organic acid, typically a chiral organic acid, for example mandelic acid which is used to precipitate the (1S, 4S) isomer. The racemisation is optionally performed in the presence of the organic or inorganic acid.

Isomerisation systems used to isomerise the C-4 chiral centre include base catalysed isomerisation systems, acid catalysed isomerisation systems and hydrogenation isomerisation systems.

Base catalysed isomerisation may be carried out by using inorganic or organic bases. Strong bases can be used but are not essential; in the context of the present invention a strong base is one which is as strong or stronger than a metal alkoxide such as sodium methoxide. Examples of organic bases that may be used include metal alkoxides, metal amides, dimsyl or trityl metal salts, quaternary ammonium salts and the like. Preferred organic bases include metal alkoxides, more preferably alkali metal alkoxides. More preferably the base is an alkali metal $C_{1-6}$ alkoxide. Sodium methoxide, sodium ethoxide and potassium tert-butoxide are preferred with potassium tert-butoxide being particularly preferred.

Conventionally in processes for isomerisation of the C-4 position, such as that described in EP0575507, a strong base such as potassium tert-butoxide is required. We have found that base catalysed isomerisation of the C-4 position can be achieved by using a mild base, i.e. a base which is at least an order of magnitude weaker than an alkoxide base. This has significant advantages in terms of cost, handling and processing of waste streams. Thus in a particularly preferred alternative embodiment the base catalysed isomerisation uses a mild base. A mild base in the context of the present invention is a base which is the same as or weaker than an alkali metal hydroxide. Preferred mild bases include quaternary ammonium salts, more preferably quaternary ammonium hydroxides, such as for example tetrabutylammonium hydroxide. More preferably the base is a quaternary $C_{1-6}$ alkyl, or aryl or mixed $C_{1-6}$ alkyl aryl ammonium hydroxide, with tetrabutyl ammonium hydroxide being preferred.

In another alternative embodiment, the mild base is a Group IA metal carbonate or hydroxide. Sodium carbonate or sodium hydroxide are particularly preferred bases of this type. In yet another alternative embodiment, the base is metal hydride, complex metal hydride or an organolithium base. Sodium hydride, alkyl lithiums such as butyl lithium and lithium diisopropylamine are examples of bases of this type which are suitable.

In an alternative preferred embodiment, the base is a polymeric base. The base may be immobilised on a polymeric support. The base can thus be supported in a column in the form of an ion exchange resin. Dowex® ion exchange resins (available from The Dow Chemical Company), Amberlyst® and Sephadex® (both available from Sigma-Aldrich Co). The resins are in hydroxide, i.e. alkaline form. Polymeric bases can be used in both a batch and a continuous process according to the invention. One particular benefit of using a polymeric base is that it is then possible to operate the process in a continuous manner. The material for racemisation can be cycled round a loop containing the base on a polymeric support with desired material being recovered after isomerisation of the other chiral centre and the remainder being recycled and repeatedly exposed to the polymeric support. The resins are ideally contained within a column. Thus in this embodiment, a continuous flow apparatus includes a vessel containing a supported transition metal catalyst to isomerise the C-1 position and a supported base, preferably on a polymeric support, to isomerise the C-4 position. Once both centres have been isomerised, the desired (1S,4S) sertraline product is separated from the product stream and the remainder of the material returned to the circuit for isomerisation.

The continuous reactor may comprise one or several vessels, for example arranged vertically, horizontally or inclined. The reactants may be fed directly to the reactor or via a separate mixing device. Suitably the reactor is a preferably substantially tubular through-flow vessel or pipe, most preferably comprising means for mixing the reactants in a substantially uniform manner. Such means for mixing are described in eg U.S. Pat. No. 6,790,427.

The purification and recovery steps of the present invention are conducted continuously, such that the fluid stream is fed continuously to each isomerisation vessel in a sequential manner. Each vessel contains the relevant isomerisation reactant(s), maintained at the preferred temperature and pressure. The stream is allowed to continuously react to form a mixture of all four isomers. The resulting mixture of isomers is continuously withdrawn from the vessel. The mixture of isomers of sertraline are separated in the conventional manner as described in WO2005/023752. Thus sertraline is separated from its trans isomers by crystallisation. Isolation of sertraline from its 1R,4R enantiomer is achieved by selective precipitation with a chiral entity such as mandelic acid. The crystals from the mixture are continuously separated from the solution and the mother liquor containing one, two or three of the other isomers is recycled back to the vessel. The crystals may be separated from the solution by means known in the art, such as filtration and centrifugation.

The process of the invention can suitably employ a basic ion exchange resin such as Amberlit® (IRA-400 (OH) resin, Amberlyst® A-26 or Dowex® 1×8 resin (after exchange with hydroxide ion) in an organic solvent. This procedure results in a high degree of isomerisation with no substantial hydrolysis or other reaction occurring.

In the method of the present invention, one innovative feature resides in combining continuous isomerisation with continuous separation of the resulting sertraline in a process in which the feed solution is continuously recycled. Feed solution is continuously supplied to the process at the same rate at which sertraline is produced in the reactor.

When alkali metal alkoxides are used preferably a mole ratio of about 5% to about 120%, preferably 10% to 20%, with respect to the amine is employed.

When quaternary ammonium hydroxides are used preferably a mole ratio of about 5% to about 200%, preferably 100% to 120%, with respect to the amine is employed.

The solvent for the isomerisation reaction is preferably an organic solvent. Organic solvents include acyclic or cyclic alcohols, acyclic or cyclic ethers, such as diisopropyl ether, tert-butyl methyl ether, tetrahydrofuran, 1,4-dioxane, and the like; aromatic hydrocarbons such as toluene, xylenes, and the like, halocarbons such as dichloromethane, dichloroethane and the like. The preferred solvents are ethers such as methanol, ethanol, dichloromethane, tetrahydrofuran and 1,4-dioxane and hydrocarbons such as toluene. In one embodiment, the solvent is a non-polar organic solvent. More preferably the solvent is a non-polar aromatic solvent as this leads to particularly good results for the C-1 isomerisation reaction. The most preferred solvent is toluene.

The isomerisation reaction may be carried out in a one phase solvent system or a multi-phase solvent system. When a multi-phase solvent system is employed, preferably the system is a two-phase system. More preferably, one of the phases of a multi-phase system is water or aqueous phase.

The isomerisation reaction is typically carried out at elevated temperature, for example at temperatures from about room temperature (20° C.) up to temperatures of up to 140C. Preferably the isomerisation reaction is carried out at temperature over 20C, more preferably from 30 to 110C. and most preferably from 40C to 90C.

The reaction times for the isomerisation reaction may vary. Typically reaction times of from 1 to 10 h, preferably from 1 to 3 h, are employed.

After the reaction is completed, the reaction mixture is concentrated and an appropriate quantity of acid is added. The isomerised racemic amine is isolated by filtration.

The catalyst system used to isomerise the C-1 chiral centre comprises a transition metal catalyst and optionally a ligand. A reaction promoter is optionally present and serves to improve the yield and/or enhance the kinetics of the reaction.

Ligands which optionally may be present include alcohols, sulphides and preferably amines, especially the isomers of the substrate amine.

When a ligand is used, optionally the ligand and the transition metal catalyst may be pre-mixed or pre-coordinated prior to the reaction with the substrate. Examples of such pre-coordinated ligand and the transition metal catalysts include those catalysts disclosed in the International patent applications with publication numbers WO97/20789, WO98/42643, and WO02/44111, each of which is incorporated herein by reference, or catalysts such as bis-dicarbonyl[1-hydroxyl-2,3,4,5-tetraphenyl-cyclopentadienylruthenium (II)hydride described in Tet. Lett. 2002, 43, 4699; chlorodicarbonyl[1-(i-propylamino)-2,3,4,5-tetraphenylcyclopentadienylruthenium(II) described in J. Am. Chem. Soc. 2003, 125, 11494; and pincer complexes such as bis-1,3-ditertbutylphosphinomethyl-dihydroiridium-2-benzene described in J. Mol. Catal. A Chemical 189, 2002, 119.

Transition metal catalysts include transition metal halides and transition metal halide complexes. Preferably, the transition metal catalyst is a transition metal halide or transition metal halide complex based on the transition metals in Group VIII of the Periodic Table, especially ruthenium, rhodium, palladium or iridium. Most preferably the catalyst is an iridium catalyst.

More preferably, the transition metal catalyst is a transition metal halide complex of the formula $M_nX_pY_r$ wherein M is a transition metal;

each X is independently selected from the group comprising: a halide; CO and OH;

Y is a neutral optionally substituted hydrocarbyl complexing group, or an optionally substituted cyclopentadienyl complexing group; and n, p and r are integers.

Although transition metal catalyst is believed to be substantially as represented in the above formula, in some circumstances the transition metal catalyst may also exist as a dimer, trimer or some other polymeric species.

Halides which may be represented by X include chloro, bromo and iodo. Thus each X can be independently selected from: fluoro, chloro, bromo and iodo. Preferably, each X is the same. More preferably, each X is iodo.

Metals which may be represented by M in the above formula include metals which are capable of catalysing transfer hydrogenation. Preferred metals include transition metals, more preferably the metals in Group VII of the Periodic Table, especially ruthenium, rhodium, iridium or palladium. Iridium is a particularly preferred transition metal. In an alternative embodiment, the catalyst is a transition metal catalyst based on ruthenium. A suitable catalyst is Shro's hydroxycyclopentadienyl ruthenium catalyst. In an alternate embodiment, the catalyst is palladium metal either supported, for example on barium sulphate, or unsupported.

Typically, the integers n, p, r are selected such that the transition metal halide complex is overall a neutral species. Therefore, the selection of n, p, r are directly related to the valance state of the metal and the number of halides present and the nature of the complexing group Y. For example, where Y is a negatively charged cyclopentadienyl complexing group, the number of negatively charged halides required to balance the valence state of the metal will be less than when Y is a neutral hydrocarbyl complexing group.

When the metal is ruthenium it is preferably present in valence state II. When the metal is rhodium or iridium it is preferably present in valence state I when Y is a neutral optionally substituted hydrocarbyl or a neutral optionally substituted perhalogenated hydrocarbyl ligand, and preferably present in valence state III when Y is an optionally substituted cyclopentadienyl ligand. An especially preferred metal is iridium.

The neutral optionally substituted hydrocarbyl or perhalogenated hydrocarbyl complexing group which may be represented by Y includes optionally substituted aryl and alkenyl complexing group.

Optionally substituted complexing groups which may be represented by Y may include cyclic hydrocarbyl groups which contain 1 ring or 2 or more fused rings which include cycloalkyl, aryl or heterocyclic rings. Preferably, the complexing group is an aryl group. Aryl groups are mono or polycyclic hydrocarbon groups in which one or more rings are aromatic. Examples include: phenyl, benzyl naphthyl, anthracenyl, cyclopentadienyl, and substituted cyclopentadienyl such as pentamethylcyclopentadienyl (Cp*). Preferably the aromatic group contains from 5 to 20 carbons. Most preferably the aryl group is optionally substituted cyclopentadienyl or phenyl. More preferably the aryl group contains at least one 6 membered aromatic ring. The ring or rings of the aryl complexing group are often substituted with hydrocarbyl groups. Suitable hydrocarbyl groups include $C_{1-8}$ alkyl; $C_{2-8}$ alkenyl; $C_{2-8}$ alkynyl; $C_{3-8}$ cycloalkyl; $C_{1-8}$ alkyl aryl; $C_{1-8}$ alkoxy; hydroxy; aryl (phenyl being a preferred substitute) and het; wherein each of the aforementioned groups may be optionally substituted where chemically possible by 1 to 6 groups independently selected from the group comprising: halo, CN, OH, $NO_2$, $CF_3$, OXO and $C_{1-4}$ alkyl. Preferred substituents are independently chosen at each occurrence. Substitution can be present at none, some or all of the available positions.

The substitution pattern and the number of substituents will vary and may be influenced by the number of rings present, but often from 1 to 6 hydrocarbyl substituent groups are present, preferably 2, 3 or 6 hydrocarbyl groups and more preferably 6 hydrocarbyl groups. Preferred hydrocarbyl substituents are defined above and include methyl, ethyl, isopropyl, menthyl, neomenthyl and phenyl.

Particularly when the aryl complexing group is a single aromatic ring, the complexing group is preferably benzene or a substituted benzene. When the complexing group is optionally substituted it is preferably polyhalogenated and/or polyalkylated. Most preferably it is a polyhalogenated benzene such as hexachlorobenzene or hexafluorobenzne. When the hydrocarbyl substitutents contain enantiomeric and/or diastereomeric centres, it is preferred that the enantiomerically and/or diastereomerically purified forms of these are used.

Benzene, p-cymyl, mesitylene and hexamethylbenzene are especially preferred complexing group.

Optionally substituted alkenyl complexing groups which may be represented by Y include $C_{2-30}$, and preferably $C_{6-12}$, alkenes or cycloalkenes with preferably two or more carbon-carbon double bonds, preferably only two carbon-carbon double bonds. The carbon-carbon double bonds may optionally be conjugated to other unsaturated systems which may be present, but are preferably conjugated to each other. The alkenes or cycloalkenes may be substituted preferably with hydrocarbyl substituents. When the alkene has only one double bond, the optionally substituted alkenyl complexing group may comprise two separate alkenes. Preferred hydrocarbyl substituents are defined above and include methyl, ethyl, iso-propyl and phenyl. Examples of optionally substituted alkenyl complexing groups include cyclo-octa-1,5-diene and 2,5-norbornadiene. Cyclo-octa-1,5-diene is especially preferred.

Optionally substituted cyclopentadienyl complexing groups which may be represented by Y includes cyclopentadienyl groups capable of eta-5 bonding. The cyclopentadienyl group is often substituted with from 1 to 5 hydrocarbyl groups, preferably with 3 to 5 hydrocarbyl groups and more preferably with 5 hydrocarbyl groups. Preferred hydrocarbyl substituents are defined above and include methyl, ethyl and phenyl. When the hydrocarbyl substitutents contain enantiomeric and/or diastereomeric centres, it may be advantageous that the enantiomerically and/or diastereomerically purified forms of these are used. Examples of optionally substituted cyclopentadienyl complexing groups include cyclopentadienyl, pentamethyl-cyclopentadienyl, pentaphenylcyclopentadienyl, tetraphenylcyclopentadienyl, ethyltetramethylpentadienyl, menthyltetraphenylcyclopentadienyl, neomenthyltetraphenylcyclopentadienyl, menthylcyclopentadienyl, neomenthylcyclopentadienyl, tetrahydroindenyl, menthyltetrahydroindenyl and neomenthyltetrahydroindenyl groups. Pentamethylcyclopentadienyl is especially preferred.

Transition metal halide complexes of the formula $M_nX_pY_r$ wherein M is Rh or Ir, and Y is an optionally substituted cyclopentadienyl group are preferred. Transition metal halide complexes of the formula $M_nX_pY_r$ wherein M is Ir and Y is an optionally substituted cyclopentadienyl group are most preferred. Highly preferred are transition metal iodide complexes of the formula $M_nI_pY_r$, more preferably wherein M is Ir and Y is an optionally substituted cyclopentadienyl group.

In an embodiment n is 1 or 2. Preferably n is 2.

In another embodiment p is 2 or 4. Preferably p is 4.

In a further embodiment r is 1 or 2. Preferably r is 2.

Examples of transition metal halide complexes include $Ru_2Cl_4(cymyl)_2$, $Rh_2Cl_4(CP^*)_2$, $Rh_2Br_4(CP^*)_2$, $Rh_2I_4(CP^*)_2$, $Ir_2Cl_4(CP^*)_2$, $Ru_2I_4(cymyl)_2$, $RhCl_2 Cp^*$, $RhBr_2 Cp^*$, $RhI_2CP$, and $Ir_2I_4(CP^*)_2$ wherein $Cp^*$ is a pentamethylcyclopentadienyl group.

In one preferred embodiment, the process of the invention is performed by first isomerising the C-1 position with a transitional metal catalyst. preferably this is an iridium-based catalyst. Whilst not wishing to be bound by theory, it is believed that the catalyst operates by oxidising sertraline by removal of hydrogen from the 1-position. The resulting imine is then reduced by the catalyst in a step involving return of the hydrogen to the catalyst with concomitant isomerisation of the sertraline at the 1-position. This step can be conducted with very low amounts of catalyst. In one embodiment, less than 2-0 mol % catalyst is required, more preferably less than 1.0 mol %, and most preferably less than 0.2 mol % catalyst is needed. Surprisingly, whilst the catalyst is able to leak hydrogen, i.e. to oxidise by loss of hydrogen to regenerate catalyst without returning it to the imine, we have found in practice that consequential formation of the imine does not occur to any significant degree. This means that the product remains in a relatively pure form and that catalyst consumption is minimised. Subsequently, the 4-position is isomerised using base in a non-polar solvent. Toluene is the solvent of choice.

The catalytic system may advantageously be introduced, at least in part, on a solid support or as an encapsulated system. Where the catalytic system is present on a solid support or as an encapsulated system, such supported catalyst systems may be of assistance in performing separation operations which may be required, and may facilitate the ease of cycling of materials between steps, especially when repetitions are envisaged.

Reaction promoters, which optionally may be present, include halide salts, for example metal halides. Preferred reaction promoters include bromide and especially iodide salts. Highly preferred are potassium iodide and caesium iodide.

In a further aspect of the present invention, the corresponding imines derived by dehydrogenation of the starting amines may be produced when the amines are treated with a catalyst system and optionally a reaction promoter.

Where it is desired to suppress the production of the corresponding imines derived by dehydrogenation of the starting amines, the use of hydrogen acceptors and/or hydrogen donors may advantageously be employed.

Hydrogen acceptors which may be present in the process of the present invention include the proton from an acid, oxygen, aldehydes and ketones, imines and imminium salts, readily hydrogenatable hydrocarbons, dyes, clean oxidising agents, carbonates, bicarbonates and any combination thereof.

The proton may emanate from any convenient and compatible acid such as formic acid, acetic acid, hydrogen carbonate, hydrogen sulfate, ammonium salt or alkyl ammonium salt. Conveniently the proton may emanate from the substrate itself.

Aldehydes and ketones which may be employed as hydrogen acceptors comprise commonly from 1 to 20 carbon atoms, preferably from 2 to 15 carbon atoms, and more preferably 3 to 5 carbon atoms. Aldehydes and ketones include alkyl, aryl, hetroaryl aldehydes and ketones, and ketones with mixed alkyl, aryl or hetroaryl groups. Examples of aldehydes and ketones which may be represented as hydrogen acceptors include formaldehyde, acetone, methylethylketone and benzophenone. When the hydrogen donor is an aldehyde or ketone, acetone is especially preferred.

Readily hydrogenatable hydrocarbons which may be employed as hydrogen acceptors comprise hydrocarbons which have a propensity to accept hydrogen or hydrocarbons which have a propensity to form reduced systems. Examples of readily hydrogenatable hydrocarbons which may be employed by as hydrogen donors include quinones, dihydroarenes and tetrahydroarenes.

Clean oxidising agents which may be represented as hydrogen acceptors comprise reducing agents with a high reduction potential, particularly those having an oxidation potential relative to the standard hydrogen electrode of greater than about 0.1 eV, often greater than about 0.5 eV, and preferably greater than about 1 eV. Examples of clean oxidising agents which may be represented as hydrogen acceptors include oxidising metals and oxygen.

Dyes include Rose Bengal, Proflavin, Ethidium Bromide, Eosin and Phenolphthalein.

Carbonates and bicarbonates include alkali metal, alkaline earth metal, ammonium and quaternary amine salts of carbonate and bicarbonate.

The most preferred hydrogen acceptors are protons from acids, acetone, oxygen, the substrate amine and carbonate and bicarbonate salts.

Hydrogen donors include hydrogen, primary and secondary alcohols, primary, secondary and tertiary amines, carboxylic acids and their esters and amine salts, readily dehydrogenatable hydrocarbons, clean reducing agents, and any combination thereof.

Primary and secondary alcohols which may be employed as hydrogen donors comprise commonly from 1 to 10 carbon atoms, preferably from 2 to 7 carbon atoms, and more preferably 3 or 4 carbon atoms. Examples of primary and secondary alcohols which may be represented as hydrogen donors include methanol, ethanol, propan-1-ol, propan-2-ol, butan-1-ol, butan-2-ol, cyclopentanol, cyclohexanol, benzylalcohol, and menthol. When the hydrogen donor is an alcohol, secondary alcohols are preferred, especially propan-2-ol and butan-2-ol.

Primary secondary and tertiary amines which may be employed as hydrogen donors comprise commonly from 1 to 20 carbon atoms, preferably from 2 to 14 carbon atoms, and more preferably 3 or 8 carbon atoms. Examples of primary, secondary and tertiary amines which may be represented as hydrogen donors include ethylamine, propylamine, isopropylamine, butylamine, isobutylamine, hexylamine, diethylamine, dipropylamine, di-isopropylamine, dibutylamine, di-isobutylamine, dihexylamine, benzylamine, dibenzylamine, piperidine, (R) or (S) 6,7-dimethoxy-1-methyldihydroisoquinoline, triethylamine. When the hydrogen donor is an amine, primary amines are preferred, especially primary amines comprising a secondary alkyl group, particularly isopropylamine and isobutylamine.

Carboxylic acids or their esters or salts which may be employed as hydrogen donors comprise commonly from 1 to 10 carbon atoms, preferably from 1 to 3 carbon atoms. In certain embodiments, the carboxylic acid is advantageously a beta-hydroxy-carboxylic acid. Esters may be derived from the carboxylic acid and a $C_{1-10}$ alcohol. Examples of carboxylic acids which may be employed as hydrogen donors include formic acid, lactic acid, ascorbic acid and mandelic acid. When a carboxylic acid is employed as hydrogen donor, at least some of the carboxylic acid is preferably present as a salt. Amine salts may be formed. Amines which may be used to form such salts include both aromatic and non-aromatic amines, also primary, secondary and tertiary amines and comprise typically from 1 to 20 carbon atoms. Tertiary amines, especially trialkylamines, are preferred. Examples of amines which may be used to form salts include trimethylamine, triethylamine, di-isopropylethylamine and pyridine. The most preferred amine is triethylamine. When at least some of the carboxylic acid is present as an amine salt, particularly when a mixture of formic acid and triethylamine is employed, the mole ratio of acid to amine is commonly about 5:2. This ratio may be maintained during the course of the reaction by the addition of either component, but usually by the addition of the carboxylic acid. Other preferred salts include sodium, potassium, magnesium Readily dehydrogenatable hydrocarbons which may be employed as hydrogen donors comprise hydrocarbons which have a propensity to aromatise or hydrocarbons which have a propensity to form highly conjugated systems. Examples of readily dehydrogenatable hydrocarbons which may be employed by as hydrogen donors include cyclohexadiene, cyclohexene, tetralin, dihydrofuran and terpenes.

Clean reducing agents which may be represented as hydrogen donors comprise reducing agents with a high reduction potential, particularly those having a reduction potential relative to the standard hydrogen electrode of greater than about −0.1 eV, often greater than about −0.5 eV, and preferably greater than about −1 eV. Examples of clean reducing agents which may be represented as hydrogen donors include hydrazine and hydroxylamine.

The most preferred hydrogen donors are (R) or (S) 6,7-dimethoxy-1-methyldihydroisoquinoline, propan-2-ol, butan-2-ol, triethylammonium formate, sodium formate, potassium formate and a mixture of triethylammonium formate and formic acid.

Although gaseous hydrogen may be present, the process is normally operated in the absence of gaseous hydrogen since it appears to be unnecessary.

Typically, inert gas sparging may be employed.

Suitably treatment with a catalyst system and optionally a reaction promoter is carried out at temperatures in the range of from 10C to plus 180° C., preferably from 20 to plus 110° C. and more preferably from 40 to plus 80° C.

The initial concentration of the substrate amines, is suitably in the range 0.05 to 3.0 and, for convenient larger scale operation, can be for example up to 6.0 more especially 0.75 to 2.0, on a molar basis. The molar ratio of the substrate to the catalyst system is suitably no less than 50:1 and can be up to 50000:1, preferably between 250:1 and 5000:1 and more preferably between 500:1 and 2500:1.

If a reaction promoter is present, the reaction promoter is preferably employed in a molar excess over the catalyst, especially from 4 to 1000 fold or, if convenience permits, greater, for example up to 5000 fold.

If a hydrogen donor and/or acceptor is present, the hydrogen donor and/or acceptor is preferably employed in a molar excess over the substrate amines, especially from 5 to 20 fold or, if convenience permits, greater, for example up to 500 fold.

Reaction times for the treatment with a catalyst system and optionally a reaction promoter are typically in the range of from 1.0 min to 24 h, especially up to 8 h and conveniently up to 3 h. After reaction, the mixture is worked up by standard procedures, for example procedures that may involve the addition of an organic acid.

A reaction solvent may be present during the treatment with a catalyst system and optionally a reaction promoter, for example alcohols such as methanol or ethanol, acyclic or cyclic ethers, such as diisopropyl ether, tert-butyl methyl ether, tetrahydrofuran, 1,4-dioxane, and the like; aromatic hydrocarbons such as toluene, xylenes, and the like, halocarbons such as dichloromethane, dichloroethane and the like, dimethylformamide, acetonitrile. Usually it is preferred to operate in substantial absence of water, but water does not appear to unduly inhibit the reaction. If the substrate amine or the reaction solvent is not miscible with water and the desired product is water soluble, it may be desirable to have water present as a second phase. The concentration of substrate may be chosen to optimise reaction time, yield and de-enrichment of enantiomeric excess. The preferred solvents are ethers such as methanol, ethanol, dichloromethane, tetrahydrofuran and 1,4-dioxane and hydrocarbons such as toluene. The most preferred solvent is toluene.

When treatments (1) and (2) occur are carried out together, in a single step, preferably the solvent employed is toluene.

Advantageously, the process of the present invention may find use in recycling unwanted isomers obtained from chiral processes, such as chiral separations, chemical and enzymic chiral resolutions and the likes. Typically, in chiral separations or resolutions, racemic mixtures are subjected to physical, chemical or biochemical treatments which result in the separation of a desired enantiomer or enantiomeric product while often leaving behind an unreacted or unwanted enantiomers or enantiomeric bi-products. The process of the present invention provides a method for converting the unreacted enantiomers to usable feedstocks containing wanted enantiomers.

The invention is illustrated by the following Examples.

EXAMPLE 1

Racemisation of (1S, 4S)—N-Methyl-4-(3,4-dichlorophenyl)-1,2,3,4-tetrahydro-1-naphthalenamine

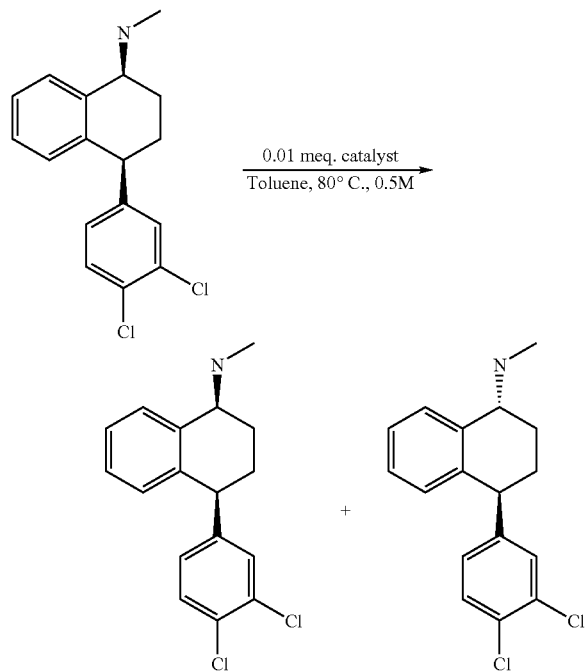

(1S, 4S)—N-Methyl-4-(3,4-dichlorophenyl)-1,2,3,4-tetrahydro-1-naphthalenamine (209 mg, 0.68 mmol) was dissolved in toluene (1.5 ml, 0.45M), under a nitrogen atmosphere. Potassium iodide (113 mg, 0.68 mmol) was then added, followed by [IrCp*Cl$_2$]$_2$ (5 mg, 6.82 μmol) and the reaction mixture heated at 80° C. for 1.5 h. The reaction mixture was then cooled down to room temperature, quenched with an aqueous solution of phosphate buffer (pH7, 5 ml), extracted with dichloromethane (5 ml), dried (Na$_2$SO$_4$) and concentrated to dryness to give a colourless solid, which was then analysed by chiral GC and shown to be a mixture of the cis-(1S, 4S)- and trans-(1R, 4S)- isomers in a ratio of 63/37 respectively.

EXAMPLE 2

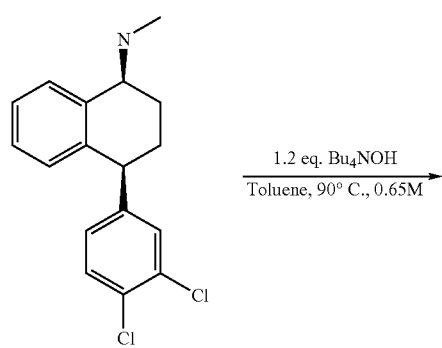

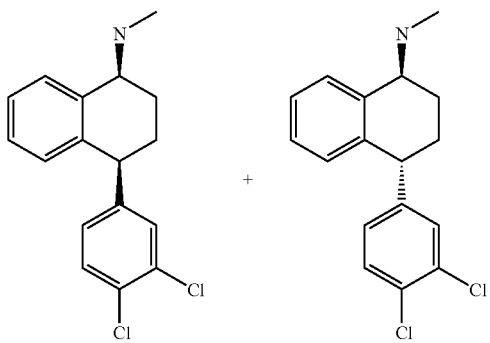

(1S, 4S)—N-Methyl-4-(3,4-dichlorophenyl)-1,2,3,4-tetrahydro-1-naphthalenamine (196 mg, 0.64 mmol) was dissolved in toluene (970 μl, 0.66M), under a nitrogen atmosphere. Tetrabutylammonium hydroxide (513 μl, 0.77 mmol) was then added and the reaction mixture heated at 90° C. for 48 h. The reaction mixture was then cooled down to room temperature, quenched with water (5 ml), extracted with dichloromethane (5 ml), dried (Na$_2$SO$_4$) and concentrated under reduced pressure to give an orange oil. Analysis of this oil by chiral GC showed the reaction gave a mixture of isomers in the ratio 55.8/0.5/1.3/42.4 assigned to the cis-(1S, 4S)-, cis-(1R, 4R)-, trans-(1R, 4S)- and trans-(1S, 4R) compounds respectively.

EXAMPLE 3

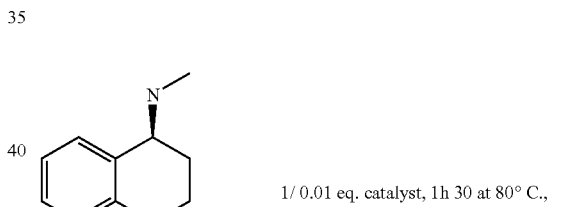

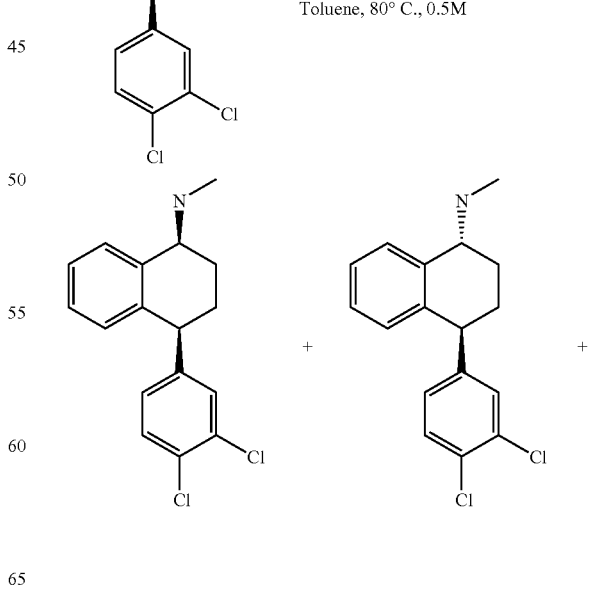

-continued

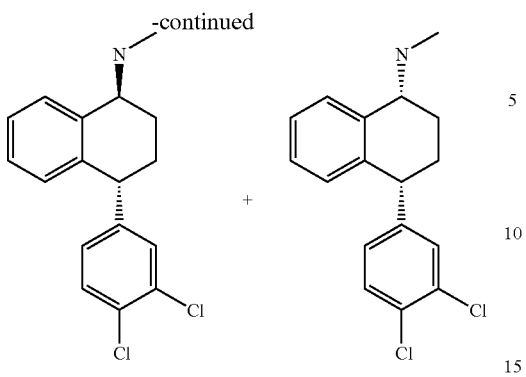

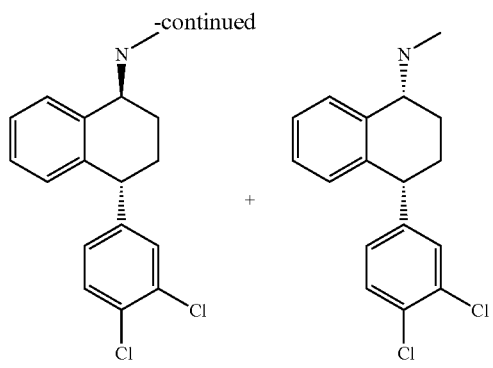

(1S, 4S)—N-Methyl-4-(3,4-dichlorophenyl)-1,2,3,4-tetrahydro-1-naphthalenamine (200 mg, 0.65 mmol) was dissolved in toluene (1.4 ml, 0.46M) under nitrogen atmosphere. Potassium iodide (108 mg, 0.65 mmol) was then added, followed by [IrCp*Cl$_2$]$_2$ (5 mg, 6.50 µmol) and the reaction mixture heated at 80° C. for 1.5 h. Tetrabutylammonium hydroxide (544 µl, 0.78 mmol) was then added and the reaction mixture heated at 80° C. for 48 h. The reaction mixture was then cooled down to room temperature, quenched with an aqueous solution of phosphate buffer (pH7, 5 ml), extracted with dichloromethane (5 ml), dried (Na$_2$SO$_4$) and concentrated under reduced pressure to give a brown oil, which was then analysed by chiral GC and the reaction shown to give a mixture of isomers in a ratio of 32.7/23.7/18.9124.7 assigned to the cis-(1S, 4S)-, cis-(1R, 4R)-, trans-(1R, 4S)- and trans-(1S,4R)-compounds respectively.

EXAMPLE 4

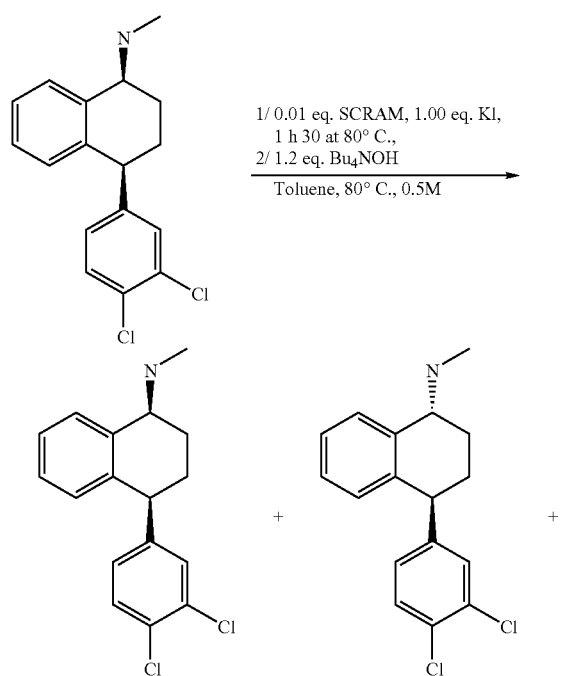

(1S, 4S)—N-Methyl-4-(3,4-dichlorophenyl)-1,2,3,4-tetrahydro-1-naphthalenamine (108 mg, 0.35 mmol) was dissolved in dioxane (0.8 ml, 0.46M), and put under nitrogen atmosphere. Potassium iodide (59 mg, 0.35 mmol) was then added, followed by [IrCp*Cl$_2$]$_2$ (3 mg, 3.501 mmol) and the reaction mixture heated at 80° C. for 1.5 h. Tetrabutylammonium hydroxide (295 µl, 0.42 mmol) was then added and the reaction mixture heated at 80° C. for 48 h. The reaction mixture was then cooled down to room temperature, quenched with an aqueous solution of phosphate buffer (pH7, 5 ml), extracted with dichloromethane (5 ml), dried (Na$_2$SO$_4$) and concentrated under reduced pressure to give a brown oil, which was then analysed by chiral GC and the reaction shown to give a mixture of isomers in a ratio of 53.318.3/27.7110.7 assigned to the cis-(1S, 4S)-, cis-(1R, 4R)-, trans-(1R, 4S)- and trans-(1S, 4R)-compounds, respectively.

I claim:

1. A process for isomerising the C-1 position of N-methyl-4-(3,4-dichlorophenyl)-1,2,3,4-tetrahydro-1-naphthaleneamine using a transition metal catalyst and optionally a promoter.

2. The process of claim 1 for obtaining (1S,4S)—N-methyl-4-(3,4-dichlorophenyl)-1,2,3,4-tetrahydro-1-naphthaleneamine from at least one isomer or a mixture of isomers selected from (1R,4R)—N-methyl-4-(3,4-dichlorophenyl)-1,2,3,4-tetrahydro-1-naphthaleneamine, (1S,4R)—N-methyl-4-(3,4-dichlorophenyl)-1,2,3,4-tetrahydro-1-naphthaleneamine, or (1R,4S)—N-methyl-4-(3,4-dichlorophenyl)-1,2,3,4-tetrahydro-1-naphthaleneamine the process comprising treating the isomer or mixture of isomers with (1) a reaction system operative to isomerise the C-4 position; and (2) a transition metal catalyst system and optionally a reaction promoter operative to isomerise the C-1 position.

3. The process of claim 2, wherein treatments (1) and (2) are carried out sequentially, in separate steps, and in any order, or are carried out together, in a single step.

4. The process of claim 2, wherein the process is operated as a continuous process.

5. The process of claim 2, wherein the reaction system operative to isomerise the C-4 position is a base catalysed isomerisation system, an acid catalysed isomerisation system or a hydrogenation isomerisation systems.

6. The process of claim 5, wherein the isomerising system is a base catalysed isomerisation system.

7. The process of claim 6, wherein the base catalysed isomerisation system comprises a polymeric base.

8. The process of claim 6, wherein the base catalysed isomerisation system comprises treatment with an inorganic or organic base, metal alkoxide, metal amide, dimsyl or trityl metal salt, quaternary ammonium salt, quaternary ammonium hydroxide, or tetrabutylammonium hydroxide.

9. The process of claim 2, wherein the catalyst system comprises a transition metal selected from Group VIII and optionally a ligand.

10. The process of claim 2, wherein the transition metal catalyst is a transition metal halide complex of the formula $M_nX_pY_r$ wherein M is a transition metal;

each X is independently selected from the group comprising: a halide, CO and OH;

Y is a neutral optionally substituted hydrocarbyl complexing group, or an optionally substituted cyclopentadienyl complexing group; and n, p and r are integers.

11. The process of claim 10, wherein X is I.

12. The process of claim 10, wherein M is Rh or Ir, and Y is an optionally substituted cyclopentadienyl group.

13. The process of claim 10, wherein X is I, M is Rh or Ir, and Y is an optionally substituted cyclopentadienyl group.

14. The process of claim 2, further comprising a reaction promoter.

15. The process of claim 14, wherein the reaction promoter is a halide salt.

16. The process of claim 15, wherein the halide salt is a metal halide.

17. The process of claim 16, wherein the metal halide is potassium or cesium iodide.

18. The process of claim 2, wherein the initial reaction mixture comprises predominantly the cis (1R,4R) stereoisomer of sertraline, with respect to any other individual isomer that may be present.

19. The process of claim 2, wherein the initial reaction mixture comprises predominantly trans stereoisomers of sertraline with respect to any cis isomer present.

20. The process of claim 2, wherein during or after the treatments (1) and (2), the (1S,4S)-isomer is separated from the reaction mixture, and thereafter or simultaneously, any unwanted (1S,4R), (1R,4R) or (1R, 4S) isomers are recycled by repeating treatments (1) and (2) in an iterative procedure.

* * * * *